United States Patent [19]

Prendergast

[11] Patent Number: 6,140,465
[45] Date of Patent: Oct. 31, 2000

[54] BAU, A BIN1 INTERACTING PROTEIN, AND USES THEREFOR

[75] Inventor: George C. Prendergast, Bala Cynwyd, Pa.

[73] Assignee: The Wistar Institute of Anatomy and Biology, Philadelphia, Pa.

[21] Appl. No.: 09/344,889

[22] Filed: Jun. 25, 1999

Related U.S. Application Data

[63] Continuation of application No. 08/919,145, Aug. 27, 1997, Pat. No. 5,958,753
[60] Provisional application No. 60/025,482, Aug. 29, 1997.
[51] Int. Cl.$^7$ .......................... A61K 38/00; A61K 38/04; C07K 1/00
[52] U.S. Cl. .......................... 530/324; 530/330; 530/350
[58] Field of Search ...................... 435/91.3, 6; 530/350, 530/324, 330

[56] References Cited

U.S. PATENT DOCUMENTS

| | | | |
|---|---|---|---|
| 5,605,830 | 2/1997 | Prendergast | 435/325 |
| 5,723,581 | 3/1998 | Prendergast | 530/350 |

FOREIGN PATENT DOCUMENTS

| | | |
|---|---|---|
| WO 84/04537 | 11/1984 | WIPO . |
| WO 96/34627 | 11/1996 | WIPO . |
| WO 98/08866 | 3/1998 | WIPO . |
| WO 98/55151 | 12/1998 | WIPO . |

OTHER PUBLICATIONS

M.D. Cole, "The myc Oncogene: its Role in Transformation and Differentiation," *Ann. Rev. Genet.*, 20:361–384 (1986).
Evan and Littlewood, "The Role of c–myc in Cell Growth," *Curr. Opin. Genet. Dev.*, 3:44–49 (1993).
M. Eilers et al., "Chimaeras of Myc Oncoprotein and Steroid Receptors Cause Hormone–Dependent Transformation of Cells", *Nature*, 340:66–68 (Jul. 6, 1989).
R. Heikkila et al., "A c–myc Antisense Oligodeoxynucleotide Inhibits Entry into S Phase but not Progress from $G_0$ to $G_1$," *Nature*, 328:445–448 (Jul. 30, 1987).
J.T. Holt et al., "An Oligomer Complementary to c–myc mRNA Inhibits Proliferation of HL–60 Promyelocytic Cells and Induces Differentiation," *Mol. Cell. Biol.*, 8:963–973 (Feb. 1988).
K.D. Hanson et al., "Effects of c–myc Expression of Cell Cycle Progression," *Mol. Cell. Biol.*, 14:5748–5755 (Sep. 1994).
D.S. Askew et al., "Constitutive c–myc Expression in an IL–3–dependent Myeloid Dell Line Suppresses Cell Cycle Arrest and Accelerates Apoptosis," *Oncogene*, 6:1915–1922 (Oct. 1991).
G.I. Evan et al., "Induction of Apoptosis in Fibroblasts by c–myc Protein," *Cell*, 69:119–128 (Apr. 3, 1992).
D. Sakamuro et al., "c–Myc Induces Apoptosis in Epithelial Cells by Both p53–dependent and p53–independent Mechanisms," *Oncogene*, 11:2411–2418 (1995).
A. Levine, "The Tumor Suppressor Genes," *Ann. Rev. Biochem.*, 62:623–651 (1993).
D. Sakamuro et al., "BIN1 is a Novel Myc–Interacting Protein with Features of a Tumor Suppressor," *Nature Genet.*, 14:69–77 (Sep. 14, 1996).
D. Negorev et al., "The Bin1 Gene Localizes to Human Chromosome 2q14 by PCR Analysis of Somatic Cell Hybrids and Fluorescence in Situ Hybridization," *Genomics*, 33:329–331 (Apr. 1996).
M.L. Cher et al., "Genetic Alterations in Untreated Metastases and Androgen–independent Prostate Cancer Detected by Comparative Genomic Hybridization and Allelotyping," *Cancer Res.*, 56:3091–3102 (Jul. 1, 1996).
R. Wechsler–Reya et al., "The Putative Tumor Suppressor BIN1 is a Short–Lived Nuclear Phosphoprotein, the Localization of which is Altered in Malignant Cells," *Cancer Res.*, 57:3258–3263 (Aug. 1, 1997).
Hardwick and Murray, "Mad 1 p, a Phosphoprotein Component of the Spindle Assembly Checkpoint in Budding Yeast," *J. Cell. Bio.*, 131:709–720 (Nov. 1995).
T. Hudson, "Human STSs Derived from Sequences in dbEST and the Unigene Collection", Database on MPSRCH, Genbank, Accession No. G24494 (1995).
G. Prendergast et al., "A New Bind for Myc," *TIG*, 9(3):91–97 (Mar. 1992).
A. Ritonja et al., "Amino Acid Sequence of the Intracellular Cysteine Proteinase Inhibitor Cystatin B from Human Liver," Biochem. Biophys. Res. Comm., 131(3):1187–1192 (Sep. 30, 1985).
Molecular Sigma Biology (catalog), p. 54 (1985).

*Primary Examiner*—Bradley L. Sisson
*Attorney, Agent, or Firm*—Howson and Howson

[57] ABSTRACT

A murine cDNA clone encoding a BIN1-Associated U1-specific protein (Bau) are provided. Also provided are methods of using the nucleic acid sequences, polypeptides, and antibodies directed against same in the diagnosis and treatment of cancers, hyperplastic disease states, or degenerative diseases.

2 Claims, 7 Drawing Sheets

FIGURE 1A

```
GGGGTGACGT GGCCATTGAG GTCTTTGAGC TGCCTGAGAA CGAGGAC ATG TTT         53
                                                    Met Phe
                                                     1

TCC CCA TCT GAC CTG GAC ACA AGC AAG CTC AGC CAC AAG TTC AAA         98
Ser Pro Ser Asp Leu Asp Thr Ser Lys Leu Ser His Lys Phe Lys
         5                   10                  15

GAG TTG CAA ATC AAA CAT GCA GTT ACA GAA GCA GAG ATT CAA AAA        143
Glu Leu Gln Ile Lys His Ala Val Thr Glu Ala Glu Ile Gln Lys
         20                  25                  30

TTG AAG ACC AAG CTT CAA GCA TCC GAA AAT GAG AAA GTA AGG TGG        188
Leu Lys Thr Lys Leu Gln Ala Ser Glu Asn Glu Lys Val Arg Trp
         35                  40                  45

GAA CTA GAA AAG AAC CAA CTG CAA CAG AAT ATA GAA GAG AAT AAA        233
Glu Leu Glu Lys Asn Gln Leu Gln Gln Asn Ile Glu Glu Asn Lys
         50                  55                  60

GAA CGG ATG CTG AAG TTG GAG AGC TAC TGG ATC GAG GCT CAG ACA        278
Glu Arg Met Leu Lys Leu Glu Ser Tyr Trp Ile Glu Ala Gln Thr
         65                  70                  75

TTA TGT CAT ACG GTG AAT GAG CAT CTC AAA GAG ACT CAG AGC CAG        323
Leu Cys His Thr Val Asn Glu His Leu Lys Glu Thr Gln Ser Gln
         80                  85                  90

TAC CAA GCC CTG GAA AAG AAA TAC AAC AAA GCA AAG AAG CTG ATC        368
Tyr Gln Ala Leu Glu Lys Lys Tyr Asn Lys Ala Lys Lys Leu Ile
         95                  100                 105

AAA GAC TTC CAG CAA AAA GAG CTC GAT TTC ATC AAG AGA CAG GAA        413
Lys Asp Phe Gln Gln Lys Glu Leu Asp Phe Ile Lys Arg Gln Glu
         110                 115                 120

GTA GAA AGA AAG AAG CGG GAG GAG GTG GAA AAG GCT CAC CTG CTT        458
Val Glu Arg Lys Lys Arg Glu Glu Val Glu Lys Ala His Leu Leu
         125                 130                 135

GAA GTC CAA GGC CTG CAA GTT CGG ATT AGA GAT TTG GAG GCT GAG        503
Glu Val Gln Gly Leu Gln Val Arg Ile Arg Asp Leu Glu Ala Glu
         140                 145                 150

GTG TTC AGA CTA CTA AAG CAA AAT GGG ACC CAG GTT AAC AAC AAC        548
Val Phe Arg Leu Leu Lys Gln Asn Gly Thr Gln Val Asn Asn Asn
         155                 160                 165

AAC AAC ATC TTT GAG AGA AGA CCA TCT CCC GGG GAA GTC TCG AAA        593
Asn Asn Ile Phe Glu Arg Arg Pro Ser Pro Gly Glu Val Ser Lys
         170                 175                 180
```

FIGURE 1B

```
GGA GAC ACT ATG GAG AAT GTG GAA GTC AAG CAA ACA TCC TGT CAG    638
Gly Asp Thr Met Glu Asn Val Glu Val Lys Gln Thr Ser Cys Gln
        185                 190                 195

GAC GGC TTG AGC CAA GAC CTG AAT GAA GCA GTC CCA GAG ACA GAG    683
Asp Gly Leu Ser Gln Asp Leu Asn Glu Ala Val Pro Glu Thr Glu
        200                 205                 210

CGC CTG GAT TCG AAA GCA TTG AAA ACC CGG GCC CAG CTC TCT GTG    728
Arg Leu Asp Ser Lys Ala Leu Lys Thr Arg Ala Gln Leu Ser Val
        215                 220                 225

AAG AAC AGG CGC CAG AGG CCC ACA AGG ACA CGG CTC TAT GAC AGC    773
Lys Asn Arg Arg Gln Arg Pro Thr Arg Thr Arg Leu Tyr Asp Ser
        230                 235                 240

GTC AGC TCA ACT GAT GGG GAG GAC AGC CTG GAG AGG AAG GTG AGC    818
Val Ser Ser Thr Asp Gly Glu Asp Ser Leu Glu Arg Lys Val Ser
        245                 250                 255

ACT CTC AAT GGC TGG CAG ACT CTT GCA GAG TGT CGT TGT CCA CCA    863
Thr Leu Asn Gly Trp Gln Thr Leu Ala Glu Cys Arg Cys Pro Pro
        260                 265                 270

GTG TAT TTA TTG AAC GTG ATA GCG GTT TTA CTG ATC TGT GCC TTA    908
Val Tyr Leu Leu Asn Val Ile Ala Val Leu Leu Ile Cys Ala Leu
        275                 280                 285

CTT GGA AGA AAG TCT CCC
926 Leu Gly Arg Lys Ser Pro
        290
```

FIGURE 2

```
GAG ATC AGA GTG AAC CAT GAG CCA GAG CCG GCC AGT GGG GCC TCA     45
Glu Ile Arg Val Asn His Glu Pro Glu Pro Ala Ser Gly Ala Ser
 1               5                  10                  15

CCC GGG GCT GCC ATC CCC AAG TCC CCA TCT CAG CCA GCA GAG GCC     90
Pro Gly Ala Ala Ile Pro Lys Ser Pro Ser Gln Pro Ala Glu Ala
                20                  25                  30

TCC GAG GTG GTG GGT GGA GCC CAG GAG CCA GGG GAG ACA GCA GCC    135
Ser Glu Val Val Gly Gly Ala Gln Glu Pro Gly Glu Thr Ala Ala
                35                  40                  45

AGT GAA GCA ACC TCC AGC TCT CTT CCG GCT GTG GTG GTG GAG ACC    180
Ser Glu Ala Thr Ser Ser Ser Leu Pro Ala Val Val Val Glu Thr
                50                  55                  60

TTC TCC GCA ACT GTG AAT GGG GCG GTG GAG GGC AGC GCT GGG ACT    225
Phe Ser Ala Thr Val Asn Gly Ala Val Glu Gly Ser Ala Gly Thr
                65                  70                  75

GGA CGC TTG GAC CTG CCC CCG GGA TTC ATG TTC AAG GTT CAA GCC    270
Gly Arg Leu Asp Leu Pro Pro Gly Phe Met Phe Lys Val Gln Ala
                80                  85                  90

CAG CAT GAT TAC ACG GCC ACT GAC ACT GAT GAG CTG CAA CTC AAA    315
Gln His Asp Tyr Thr Ala Thr Asp Thr Asp Glu Leu Gln Leu Lys
                95                 100                 105

GCT GGC GAT GTG GTG TTG GTG ATT CCT TTC CAG AAC CCA GAG GAG    360
Ala Gly Asp Val Val Leu Val Ile Pro Phe Gln Asn Pro Glu Glu
               110                 115                 120

CAG GAT GAA GGC TGG CTC ATG GGT GTG AAG GAG AGC GAC TGA        402
Gln Asp Glu Gly Trp Leu Met Gly Val Lys Glu Ser Asp
               125                 130
```

FIGURE 3A

```
GAATTCCGTG CTGGTTGAGC TTGCTCATCT CCTTGTGGAA GTTTTCCTCC                    50

AGGCCCGCG ATG CTC TGG AAC GTG GTG ACG GCG GGA AAG ATC GCC                 95
          Met Leu Trp Asn Val Val Thr Ala Gly Lys Ile Ala
           1               5                      10

AGC AAC GTG CAG AAG AAG CTC ACC CGC GCG CAG GAG AAG GTT CTC              140
Ser Asn Val Gln Lys Lys Leu Thr Arg Ala Gln Glu Lys Val Leu
            15                  20                  25

CAG AAG CTG GGG AAG GCA GAT GAG ACC AAG GAT GAG CAG TTT GAG              185
Gln Lys Leu Gly Lys Ala Asp Glu Thr Lys Asp Glu Gln Phe Glu
            30                  35                  40

CAG TGC GTC CAG AAT TTC AAC AAG CAG CTG ACG GAG GGC ACC CGG              230
Gln Cys Val Gln Asn Phe Asn Lys Gln Leu Thr Glu Gly Thr Arg
            45                  50                  55

CTG CAG AAG GAT CTC CGG ACC TAC CTG GCC TCC GTC AAA GCC ATG              275
Leu Gln Lys Asp Leu Arg Thr Tyr Leu Ala Ser Val Lys Ala Met
            60                  65                  70

CAC GAG GCT TCC AAG AAG CTG AAT GAG TGT CTG CAG GAG GTG TAT              320
His Glu Ala Ser Lys Lys Leu Asn Glu Cys Leu Gln Glu Val Tyr
            75                  80                  85

GAG CCC GAT TGG CCC GGC AGG GAT GAG GCA AAC AAG ATC GCA GAG              365
Glu Pro Asp Trp Pro Gly Arg Asp Glu Ala Asn Lys Ile Ala Glu
            90                  95                 100

AAC AAC GAC CTG CTG TGG ATG GAT TAC CAC CAG AAG CTG GTG GAC              410
Asn Asn Asp Leu Leu Trp Met Asp Tyr His Gln Lys Leu Val Asp
           105                 110                 115

CAG GCG CTG CTG ACC ATG GAC ACG TAC CTG GGC CAG TTC CCC GAC              455
Gln Ala Leu Leu Thr Met Asp Thr Tyr Leu Gly Gln Phe Pro Asp
           120                 125                 130

ATC AAG TCA CGC ATT GCC AAG CGG GGG CGC AAG CTG GTG GAC TAC              500
Ile Lys Ser Arg Ile Ala Lys Arg Gly Arg Lys Leu Val Asp Tyr
           135                 140                 145

GAC AGT GCC CGG CAC CAC TAC GAG TCC CTT CAA ACT GCC AAA AAG              545
Asp Ser Ala Arg His His Tyr Glu Ser Leu Gln Thr Ala Lys Lys
           150                 155                 160

AAG GAT GAA GCC AAA ATT GCC AAG GCC GAG GAG GAG CTC ATC AAA              590
Lys Asp Glu Ala Lys Ile Ala Lys Ala Glu Glu Glu Leu Ile Lys
           165                 170                 175
```

FIGURE 3B

```
GCC CAG AAG GTG TTT GAG GAG ATG AAT GTG GAT CTG CAG GAG GAG    635
Ala Gln Lys Val Phe Glu Glu Met Asn Val Asp Leu Gln Glu Glu
        180             185             190

CTG CCG TCC CTG TGG AAC AGC CGC GTA GGT TTC TAC GTC AAC ACG    680
Leu Pro Ser Leu Trp Asn Ser Arg Val Gly Phe Tyr Val Asn Thr
        195             200             205

TTC CAG AGC ATC GCG GGC CTG GAG GAA AAC TTC CAC AAG GAG ATG    725
Phe Gln Ser Ile Ala Gly Leu Glu Glu Asn Phe His Lys Glu Met
        210             215             220

AGC AAG CTC AAC CAG AAC CTC AAT GAT GTG CTG GTC GGC CTG GAG    770
Ser Lys Leu Asn Gln Asn Leu Asn Asp Val Leu Val Gly Leu Glu
        225             230             235

AAG CAA CAC GGG AGC AAC ACC TTC ACG GTC AAG GCC CAG CCC AGA    815
Lys Gln His Gly Ser Asn Thr Phe Thr Val Lys Ala Gln Pro Arg
        240             245             250

AAG AAA AGT AAA CTG TTT TCG CGG CTG CGC AGA AAG AAG AAC AGT    860
Lys Lys Ser Lys Leu Phe Ser Arg Leu Arg Arg Lys Lys Asn Ser
        255             260             265

GAC AAC GCG CCT GCA AAA GGG AAC AAG AGC CCT TCG CCT CCA GAT    905
Asp Asn Ala Pro Ala Lys Gly Asn Lys Ser Pro Ser Pro Pro Asp
        270             275             280

GGC TCC CCT GCC GCC ACC CCC GAG ATC AGA GTC AAC CAC GAG CCA    950
Gly Ser Pro Ala Ala Thr Pro Glu Ile Arg Val Asn His Glu Pro
        285             290             295

GAG CCG GCC GGC GGG GCC ACG CCC GGG GCC ACC CTC CCC AAG TCC    995
Glu Pro Ala Gly Gly Ala Thr Pro Gly Ala Thr Leu Pro Lys Ser
        300             305             310

CCA TCT CAG CCA GCA GAG GCC TCG GAG GTG GCG GGT GGG ACC CAA   1040
Pro Ser Gln Pro Ala Glu Ala Ser Glu Val Ala Gly Gly Thr Gln
        315             320             325

CCT GCG GCT GGA GCC CAG GAG CCA GGG GAG ACT TCT GCA AGT GAA   1085
Pro Ala Ala Gly Ala Gln Glu Pro Gly Glu Thr Ser Ala Ser Glu
        330             335             340

GCA GCC TCC AGC TCT CTT CCT GCT GTC GTG GTG GAG ACC TTC CCA   1130
Ala Ala Ser Ser Ser Leu Pro Ala Val Val Val Glu Thr Phe Pro
        345             350             355

GCA ACT GTG AAT GGC ACC GTG GAG GGC GGC AGT GGG GCC GGG CGC   1175
Ala Thr Val Asn Gly Thr Val Glu Gly Gly Ser Gly Ala Gly Arg
        360             365             370
```

FIGURE 3C

```
TTG GAC CTG CCC CCA GGT TTC ATG TTC AAG GTA CAG GCC CAG CAC   1220
Leu Asp Leu Pro Pro Gly Phe Met Phe Lys Val Gln Ala Gln His
        375             380             385

GAC TAC ACG GCC ACT GAC ACA GAC GAG CTG CAG CTC AAG GCT GGT   1265
Asp Tyr Thr Ala Thr Asp Thr Asp Glu Leu Gln Leu Lys Ala Gly
        390             395             400

GAT GTG GTG CTG GTG ATC CCC TTC CAG AAC CCT GAA GAG CAG GAT   1310
Asp Val Val Leu Val Ile Pro Phe Gln Asn Pro Glu Glu Gln Asp
        405             410             415

GAA GGC TGG CTC ATG GGC GTG AAG GAG AGC GAC TGG AAC CAG CAC   1355
Glu Gly Trp Leu Met Gly Val Lys Glu Ser Asp Trp Asn Gln His
        420             425             430

AAG AAG CTG GAG AAG TGC CGT GGC GTC TTC CCC GAG AAC TTC ACT   1400
Lys Lys Leu Glu Lys Cys Arg Gly Val Phe Pro Glu Asn Phe Thr
        435             440             445

GAG AGG GTC CCA TGACGGCGGG GCCCAGGCAG CCTCCGGGCG TGTGAAGAAC   1452
Glu Arg Val Pro
        450

ACCTCCTCCC GAAAAATGTG TGGTTCTTTT TTTTGTTTTG TTTTCGTTTT        1502

TCATCTTTTG AAGAGCAAAG GGAAATCAAG AGGAGACCCC CAGGCAGAGG        1552

GGCGTTCTCC CAAAGTTTAG GTCGTTTTCC AAAGAGCCGC GTCCCGGCAA        1602

GTCCGGCGGA ATTCACCAGT GTTCCTGAAG CTGCTGTGTC CTCTAGTTGA        1652

GTTTCTGGCG CCCCTGCCTG TGCCCGCATG TGTGCCTGGC CGCAGGGCGG        1702

GGCTGGGGGC TGCCGAGCCA CCATACTTAA CTGAAGCTTC GGCCGCACCA        1752

CCCGGGGAAG GGTCCTCTTT TCCTGGCAGC TGCTGTGGGT GGGGCCCAGA        1802

CACCAGCCTA GCCTGCTCTG CCCCGCAGAC GGTCTGTGTG CTGTTTGAAA        1852

ATAAATCTTA GTGTTCAAAA CAAAATGAAA CAAAAAAAAA AATGATAAAA        1902

ACTCTCAAAA AAACAAGGAA TTC                                     1925
```

BAU, A BIN1 INTERACTING PROTEIN, AND USES THEREFOR

CROSS-REFERENCE TO RELATED APPLICATION

This is a continuation of U.S. patent application Ser. No. 08/919,145, filed Aug. 27, 1997, issued Sep. 28, 1999 as U.S. Pat. No. 5,958,753, which claims the benefit of U.S. Provisional Patent Application Ser. No. 60/025,482, filed Aug. 29, 1997.

FIELD OF THE INVENTION

This invention relates generally to cancer diagnosis and therapy, and more specifically, to cancers associated with activation of the Myc oncoprotein and/or loss of Bin1 tumor suppression.

BACKGROUND OF THE INVENTION

There is a significant need for effective therapies against many types of cancers, especially carcinoma, which is often untreatable in its advanced states. Cell regulation by the Myc oncoprotein offers an attractive focus for therapeutic development. Myc is deregulated in a wide variety of cancers, including most carcinomas, through genetic and epigenetic mechanisms [M. D. Cole, *Ann. Rev. Genet.*, 20:361–384 (1986)]. Thus, Myc-regulated mechanisms are logical targets for developing novel and broadly applicable therapeutic strategies.

Myc acts at the intersection of pathways that control cell division, differentiation, and apoptosis. In normal cells, Myc is rapidly induced following mitogenic stimulation and remains elevated throughout the cell cycle [Evan and Littlewood, *Curr Opin Genet Dev.* 3: 44–49 (1993)]. Induction of Myc is sufficient to drive cell proliferation [M. Eilers, et al., *Nature*, 340: 66–8 (1989)], while inhibition of Myc can block mitogenic signals and facilitate cell differentiation [R. Heikkila, et al., *Nature*, 328: 445–448 (1987); J. T. Holt, et al., *Mol Cell Biol*, 8: 963–973 (1988); K. D. Hanson, et al., *Mol Cell Biol*, 14: 5748–5755 (1994)]. Significantly, Myc can induce apoptosis [D. S. Askew, et al., *Oncogene*, 6: 1915–1922 (1991); G. I. Evan, et al., *Cell*, 69: 119–128 (1992)], if its expression is uncoupled from the orchestration of other cell cycle regulatory events [G. I. Evan, et al., cited above]. Clinical evidence indicates that loss of the apoptotic response is associated with malignant conversion. Therefore, reactivation or derepression of this response would be desirable. Myc-activated death in epithelial cells (the precursor cell type to carcinoma) is p53-independent [D. Sakamuro, et al., *Oncogene*, 11: 2411–2418 (1995)], a useful feature because p53 function is often lost in carcinoma [Levine, *Ann Rev Biochem*, 62: 623–651 (1993)]. Thus, using Myc-activated death mechanisms is attractive, since the tumor cell could be attacked without regard to its p53 status.

Bin1 is a 451 amino acid Myc-interacting nuclear phosphoprotein [D. Sakamuro, et al., *Nature Genet*, 14: 69–77 (1996)], which has been implicated in the mechanism by which Myc induces apoptosis. Bin1 has several features of a tumor suppressor that is lost in breast and prostate carcinoma, where loss of apoptotic potential is tantamount to malignant conversion. First, Bin1 suppresses malignant cell transformation by Myc, but also by adenovirus E1A and by mutant p53, which act by Myc-independent mechanisms. Second, while normally ubiquitously expressed, Bin1 is frequently missing in breast and prostate carcinoma cell lines and primary tumors. Third, these deficits in expression appear to be functionally significant, because ectopic expression of Bin1 inhibits the growth of tumor cells which lack endogenous Bin1. Fourth, the N-terminal region of Bin1, termed the BAR domain, is closely related to a breast cancer-associated autoimmune antigen (amphiphysin) and a negative regulator of the yeast cell cycle (RVS167) [D. Sakamuro, et al., cited above.]. Finally, the human Bin1 gene maps to chromosome 2q14 [D. Negorev, et al., *Genomics*, 33: 329–331 (1996)], within a mid-2q region that is among the more frequently deleted loci in metastatic prostate cancers [M. L. Cher, et al., *Canc Res*, 56: 3091–3102 (1996)].

The murine and human BIN1 sequences, provided herein as FIGS. 2 and 3, are described in more detail in WO 96/34627. Of particular interest is the unique-1 (U1) region (located between aa 225–250) [D. Sakamuro et al, cited above; R. Wechsler-Reya, et al., *Cancer Res*, 57:3258–3263 (1997)], which mediates efficient cell growth inhibition through both Myc-dependent and Myc-independent mechanisms. U1 is encoded by exon 9 in the human Bin1 gene, located adjacent to the alternatively spliced exon 10.

There remains a need in the art for compositions and methods of regulating a deregulated Myc protein and of treating and diagnosing cancers associated with the Myc oncoprotein and/or undesirably low Bin1 levels.

SUMMARY OF THE INVENTION

In one aspect, the present invention provides a murine cDNA clone of a BIN1-Associated U1-specific protein (Bau) SEQ ID NO:1 and the polypeptide encoded thereby, SEQ ID NO:2.

In yet another aspect, the present invention provides a vector comprising a mammalian nucleic acid sequence encoding a BIN1 protein and a host cell transformed by such a vector. Alternatively, this vector may be used in gene therapy applications.

In still another aspect, the invention provides an oligonucleotide probe comprising a nucleic acid sequence as defined herein. Also provided is an antibody raised against a Bau protein or peptide thereof.

In yet a further aspect, the present invention provides a diagnostic reagent for cancers, involving Myc, inappropriately high Bau levels, or inappropriately low Bin levels, comprising an oligonucleotide probe or an antibody of the invention.

Further provided is a therapeutic reagent comprising a polypeptide, anti-idiotype antibody, or gene therapy vector of the invention.

Still another aspect of the invention provides a method of treating cancers involving Myc by administering a therapeutic reagent of the invention.

Other aspects and advantages of the present invention are described further in the following detailed description of the preferred embodiments thereof.

BRIEF DESCRIPTION OF THE DRAWINGS

FIGS. 1A–1B is a murine Bau cDNA sequence [SEQ ID NO:1] and the murine Bau polypeptide encoded thereby [SEQ ID NO:2].

FIG. 2 is a murine CDNA sequence [SEQ ID NO:3] encoding a BIN1 polypeptide [SEQ ID NO:4].

FIGS. 3A–3C is a human CDNA sequence [SEQ ID NO:5] encoding a BIN1 polypeptide [SEQ ID NO:6].

DETAILED DESCRIPTION OF THE INVENTION

Figure 4:
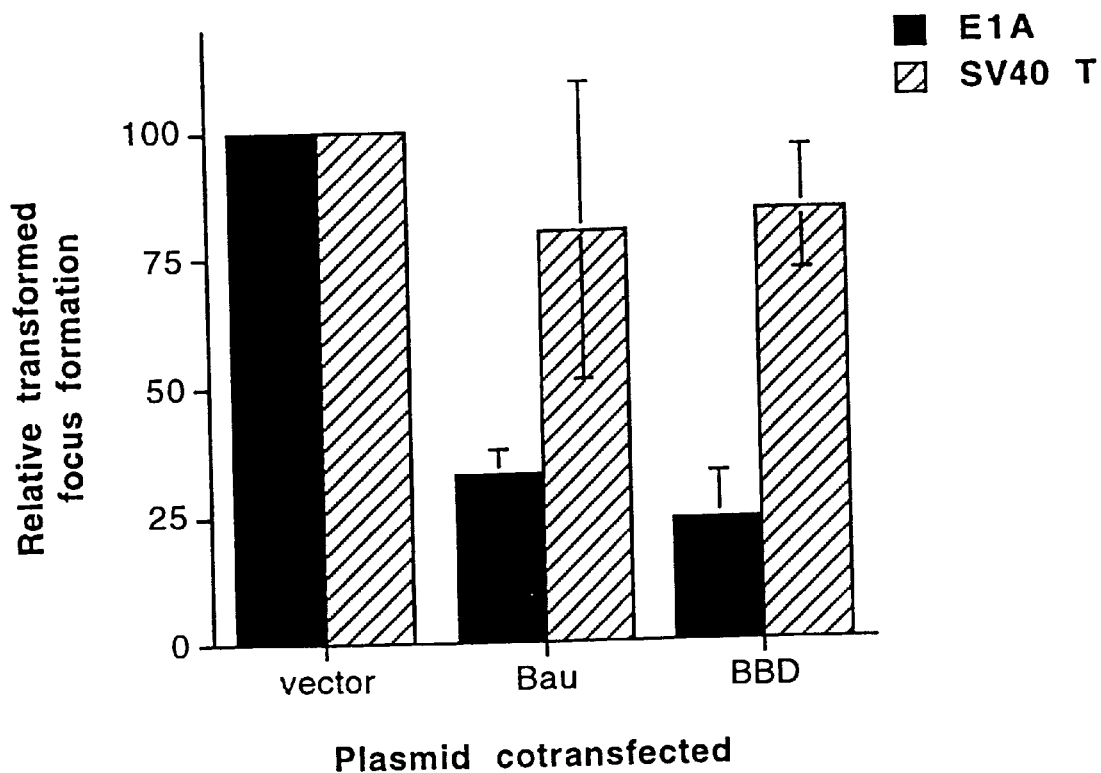
FIG. 4 is a bar chart illustrating Bau suppression of malignant transformation of rat embryo fibroblasts by the adenovirus E1a oncoprotein.

The present invention provides novel, isolated, nucleic acid Bau sequences which encode novel proteins which interact with BIN1 and bind thereto, fragments of these sequences and antibodies developed thereto. As described above briefly, BIN1 is a protein that interacts with the functionally critical Myc box regions at the N-terminus of the Myc oncoprotein and which is associated with tumor suppression and apoptosis. BIN1 is described in more detail in the International Patent Application which published as WO 96/34627 on Nov. 7, 1996 and U.S. Pat. No. 5,605,830, as well as in co-owned, co-pending U.S. patent application Ser. No. 08/652,972, which are incorporated herein by reference.

The Bau nucleic acid sequences, amino acid sequences and antibodies of the invention are useful in the detection, diagnosis and treatment of cancers or other disorders associated with inappropriate BIN1 levels and/or deregulation, deficiency or amplification of the c-Myc oncogenes. These aspects of the invention are discussed in more detail below.

I. Nucleic Acid Sequences

The present invention provides mammalian nucleic acid sequences encoding a 293 amino acid polypeptide, termed herein Bau. The nucleic acid sequences of this invention are isolated from cellular materials with which they are naturally associated.

The Bau cDNA was isolated in a yeast two hybrid screen for polypeptides that could specifically associate with the U1 domain (aa 225–250) of the human BIN1 protein [SEQ ID NO:6]. The U1 region is a functionally important region of BIN1 and has a role in protein-protein interaction. U1 contains several amino acid sequence motifs which are found in regulators of the cell cycle and chromosome function. Two ⁻10 residue motifs show relatedness to the yeast proteins p93dis1 [Nabeshima et al, *Genes Dev.*, 9:1572–1585 (1995)] and RED1 (Thompson and Roeder, *Mol. Gen. Genet.*, 218:293–301 (1989)), which are involved in chromosome segregation. An additional sequence motif is shared with a region of the SV40 virus T antigen protein (aa 5–35) which is implicated in its cellular immortalization activity [Conzen and Cole, *Oncogene*, 11:2295–2302 (1995)]. Notably, the BIN-T antigen similarity is of the form DψLXGXE [SEQ ID NO:7] (the greek psi represents a hydrophobic amino acid), which is reminiscent of the (D)LXCXE [SEQ ID NO:8] motif which mediates protein-protein interactions with the retinoblastoma (Rb) protein, an important regulator of the G1 phase of the cell cycle. A connection to Rb is intriguing, because an Rb-sized ⁻110 kD protein(s) is specifically coimmunoprecipitated with BIN1 from cell lysates by anti-BIN1 monoclonal antibodies. Further, in cell transformation experiments, U1 deletion reduced the activity of BIN1 to inhibit the oncogenic activity of MYC, and abolished the ability of BIN1 to inhibit the oncogenic activity of the adenovirus E1A oncoprotein, which is functionally related to MYC and which must inactivate Rb to transform cells. The ability of the 293 aa Bau polypeptide to inhibit E1A-mediated cell transformation, similar to BIN1, indicates its direct role in regulating U1. Taken together, the data indicates that Bau possesses anti-oncogenic activity, possibly related to apoptosis. Furthermore, the data suggests that Bau influences or mediates Bin1 activity through interactions with U1.

Thus, in one embodiment, the invention provides a Bau nucleic acid sequence which is selected from all or part of the murine cDNA clone, SEQ ID NO: 1. However, the present invention is not limited to these nucleic acid sequences.

Given the sequences of SEQ ID NO: 1, one of skill in the art can readily obtain the corresponding anti-sense strands of these cDNA and genomic sequences. Further, using known techniques, one of skill in the art can readily obtain the human sequences corresponding to these cDNA sequences or the corresponding RNA sequences, as desired.

Similarly, the availability of SEQ ID NO:1 of this invention permits one of skill in the art to obtain other species Bau homologs, by use of the nucleic acid sequences of this invention as probes in a conventional technique, e.g., polymerase chain reaction. Allelic variants of these sequences within a species (i.e., nucleotide sequences containing some individual nucleotide differences from a more commonly occurring sequence within a species, but which nevertheless encode the same protein), may also be readily obtained given the knowledge of this sequence provided by this invention.

The present invention further encompasses nucleic acid sequences capable of hybridizing under stringent conditions [see, J. Sambrook et al, *Molecular Cloning: A Laboratory Manual*, 2d ed., Cold Spring Harbor Laboratory (1989)] to the sequences of SEQ ID NO: 1, their anti-sense strands, or biologically active fragments thereof. An example of a highly stringent hybridization condition is hybridization at 2XSSC at 65° C., followed by a washing in 0.1XSSC at 65° C. for an hour. Alternatively, an exemplary highly stringent hybridization condition is in 50% formamide, 4XSSC at 42° C. Moderately high stringency conditions may also prove useful, e.g. hybridization in 4XSSC at 55° C., followed by washing in 0.1XSSC at 37° C. for an hour. An alternative exemplary moderately high stringency hybridization condition is in 50% formamide, 4XSSC at 30° C.

Also encompassed within this invention are fragments of the above-identified nucleic acid sequences. Preferably, such fragments are characterized by encoding a functional fragment of Bau, e.g., the Bin1-binding domain (nucleotides 231 to 674 of SEQ ID NO:1), an epitope, or another fragment characterized by having a desired biological activity. Generally, these oligonucleotide fragments are at least 15 nucleotides in length. However, oligonucleotide fragments of varying sizes may be selected as desired. Such fragments may be used for such purposes as performing the PCR, e.g., on a biopsied tissue sample. For example, one nucleotide fragment optimal for PCR is the fragment defined by nucleotides 231 to 674 within SEQ ID NO: 1. Other useful fragments may be readily identified by one of skill in the art by resort to conventional techniques, e.g., by computerized motif searching. Examples of such useful fragments include (with reference to SEQ ID NO:1) nt 48 to 527, which encode a coiled-coil domain; nt 312 to 362, which encode a signature motif; nt 294 to 356, which encode a cystatin motif; and nt 540 to 554, which encode a polyasparagine region.

The nucleotide sequences of the invention may be isolated by conventional uses of polymerase chain reaction or cloning techniques such as those described in obtaining the murine sequences, described below. Alternatively, these sequences may be constructed using conventional genetic engineering or chemical synthesis techniques.

According to the invention, the nucleic acid sequences [SEQ ID NO: 1] may be modified. Utilizing the sequence data in these figures and in the sequence listing, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion. Also included are allelic variations, caused by the natural degeneracy of the genetic code.

Also encompassed by the present invention are mutants of the Bau gene provided herein. Such mutants include amino terminal, carboxy terminal or internal deletions which are useful as dominant inhibitor genes. Such a truncated, or deletion, mutant may be expressed for the purpose of inhibiting the activity of the full- length or wild-type gene. These nucleic acid sequences are useful for a variety of diagnostic and therapeutic uses. Advantageously, the nucleic acid sequences are useful in the development of diagnostic probes and antisense probes for use in the detection and diagnosis of conditions characterized by inappropriate BIN1 levels, which may be associated with deregulation or amplification of c-mYc. The nucleic acid sequences of this invention are also useful in the production of mammalian, and particularly, murine and human BIN1 proteins.

II. Protein Sequences

The present invention also provides mammalian Bau polypeptides or proteins. These proteins are free from association with other contaminating proteins or materials with which they are found in nature. In one embodiment, the invention provides a murine Bau [SEQ ID NO:2] polypeptide of 293 amino acids having a predicted molecular weight (MW) 34,137.

Further encompassed by this invention are fragments of the Bau polypeptides. Such fragments are desirably characterized by having Bau biological activity, including, e.g., the ability to interact with BIN1. An example of such a fragment is aa 62 to 209, which encompasses the Bin1-binding domain. Other useful fragments may be designed or obtained in any desired length, including as small as about 8 amino acids in length. Such a fragment may represent an epitope of the protein. Further, one of skill in the art can readily identify other functional fragments, e.g., by computer motif analysis. Examples of such useful fragments include (with reference to SEQ ID NO:2), aa 1 to 160 which is a coiled-coil domain; aa 89 to 105, which is a signature motif; aa 83 to 103, which is a cystatin motif; and aa 165 to 169, which is a polyasparagine region.

Also included in the invention are analogs, or modified versions, of the proteins provided herein. Typically, such analogs differ by only one to four codon changes. Examples include polypeptides with minor amino acid variations from the illustrated amino acid sequences of Bau (FIG. 1; SEQ ID NO:2); in particular, conservative amino acid replacements. Conservative replacements are those that take place within a family of amino acids that are related in their side chains and chemical properties. Also provided are homologs of Bau. Based on the sequence information provided herein, one of skill in the art can readily obtain Bau from other mammalian species. Such analogs and homologs are typically at least about 85% homologous with SEQ ID NO: 2, and more desirably, at least about 90% homologous, as determined by sequence comparison algorithms such as WU-BLAST2 (Washington University BLAST).

Additionally, the Bau proteins [SEQ ID NO:2] of the invention may be modified, for example, by truncation at the amino or carboxy termini, by elimination or substitution of one or more amino acids, or by any number of now conventional techniques to improve production thereof, to enhance protein stability or other characteristics, e.g. binding activity or bioavailability, or to confer some other desired property upon the protein.

III. Expression

A. In Vitro

To produce recombinant Bau proteins of this invention, the DNA sequences of the invention are inserted into a suitable expression system. Desirably, a recombinant molecule or vector is constructed in which the polynucleotide sequence encoding Bau is operably linked to a heterologous expression control sequence permitting expression of the Bau protein. Numerous types of appropriate expression vectors are known in the art for mammalian (including human) protein expression, by standard molecular biology techniques. Such vectors may be selected from among conventional vector types including insects, e.g., baculovirus expression, or yeast, fungal, bacterial or viral expression systems. Other appropriate expression vectors, of which numerous types are known in the art, can also be used for this purpose.

Methods for obtaining such expression vectors are well-known. See, Sambrook et al, *Molecular Cloning. A Laboratory Manual,* 2d edition, Cold Spring Harbor Laboratory, New York (1989); Miller et al, *Genetic Engineering,* 8:277–298 (Plenum Press 1986) and references cited therein.

Suitable host cells or cell lines for transfection by this method include mammalian cells, such as Human 293 cells, Chinese hamster ovary cells (CHO), the monkey COS-1 cell line or murine 3T3 cells derived from Swiss, Balb-c or NIH mice may be used. Another suitable mammalian cell line is the CV-1 cell line. Still other suitable mammalian host cells, as well as methods for transfection, culture, amplification, screening, production, and purification are known in the art. [See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446].

Similarly bacterial cells are useful as host cells for the present invention. For example, the various strains of *E. coli* (e.g., HB101, MC1061, and strains used in the following examples) are well-known as host cells in the field of biotechnology. Various strains of *B. subtilis,* Pseudomonas, other bacilli and the like may also be employed in this method.

Many strains of yeast cells known to those skilled in the art are also available as host cells for expression of the polypeptides of the present invention. Other fungal cells may also be employed as expression systems. Alternatively, insect cells such as *Spodoptera frugipedera* (Sf9) cells may be used.

Thus, the present invention provides a method for producing a recombinant Bau protein which involves transfecting a host cell with at least one expression vector containing a recombinant polynucleotide encoding a Bau protein under the control of a transcriptional regulatory sequence, e.g., by conventional means such as electroporation. The transfected host cell is then cultured under conditions that allow expression of the Bau protein. The expressed protein is then recovered, isolated, and optionally purified from the culture medium (or from the cell, if expressed intracellularly) by appropriate means known to one of skill in the art.

For example, the proteins may be isolated in soluble form following cell lysis, or may be extracted using known techniques, e.g., in guanidine chloride. If desired, the Bau proteins of the invention may be produced as a fusion protein. For example, it may be desirable to produce Bau fusion proteins, to enhance expression of the protein in a selected host cell, to improve purification, or for use in monitoring the presence of Bau in tissues, cells or cell extracts. Suitable fusion partners for the Bau proteins of the invention are well known to those of skill in the art and include, among others, β-galactosidase, glutathione-S-transferase, and poly-histidine.

B. In Vivo

Alternatively, where it is desired that the Bau protein be expressed in vivo, e.g., for gene therapy purposes, an appropriate vector for delivery of Bau, or fragment thereof, may be readily selected by one of skill in the art. Exemplary gene therapy vectors are readily available from a variety of academic and commercial sources, and include, e.g., adeno-associated virus [International patent application No. PCT/US91/03440], adenovirus vectors [M. Kay et al, *Proc. Natl. Acad. Sci. USA*, 91:2353 (1994); S. Ishibashi et al, *J. Clin. Invest.*, 92:883 (1993)], or other viral vectors, e.g., various poxviruses, vaccinia, etc. Methods for insertion of a desired gene, e.g. Bau, and obtaining in vivo expression of the encoded protein, are well known to those of skill in the art.

IV. Antisera and Antibodies

The Bau proteins of this invention are also useful as antigens for the development of anti-Bau antisera and antibodies to Bau or to a desired fragment of a Bau protein. Specific antisera may be generated using known techniques. See, Sambrook, cited above, Chapter 18, generally, incorporated by reference. Similarly, antibodies of the invention, both polyclonal and monoclonal, may be produced by conventional methods, including the Kohler and Milstein hybridoma technique, recombinant techniques, such as described by Huse et al, *Science*, 246:1275–1281 (1988), or any other techniques known to the art.

Also encompassed within this invention are humanized and chimeric antibodies. As used herein, a humanized antibody is defined as an antibody containing murine complementary determining regions (CDRS) capable of binding to Bau or a fragment thereof, and human framework regions. These CDRs are preferably derived from a murine monoclonal antibody (MAb) of the invention. As defined herein, a chimeric antibody is defined as an antibody containing the variable region light and heavy chains, including both CDR and framework regions, from a Bau MAb of the invention and the constant region light and heavy chains from a human antibody. Methods of identifying suitable human framework regions and modifying a MAb of the invention to contain same to produce a humanized or chimeric antibody of the invention, are well known to those of skill in the art. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June 1994). Other types of recombinantly- designed antibodies are also encompassed by this invention.

Further provided by the present invention are anti- idiotype antibodies (Ab2) and anti-anti-idiotype antibodies (Ab3). Ab2 are specific for the target to which anti-Bau antibodies of the invention bind and Ab3 are similar to Bau antibodies (Ab1) in their binding specificities and biological activities [see, e.g., M. Wettendorff et al, "Modulation of anti-tumor immunity by anti-idiotypic antibodies." In *Idiotypic Network and Diseases*, ed. by J. Cerny and J. Hiernaux J, Am. Soc. Microbiol., Washington DC: pp. 203–229, (1990)). These anti-idiotype and anti-anti-idiotype antibodies may be produced using techniques well known to those of skill in the art. Such anti-idiotype antibodies (Ab2) can bear the internal image of Bau and can thus bind to Bin1 in much the same manner as Bau, and are thus useful for the same purposes as Bau.

In general, polyclonal antisera, monoclonal antibodies and other antibodies which bind to Bau as the antigen (Ab1) are useful to identify epitopes of Bau, to separate Bau from contaminants in living tissue (e.g., in chromatographic columns and the like), and in general as research tools and as starting material essential for the development of other types of antibodies described above. Anti-idiotype antibodies (Ab2) are useful for binding BIN1 and thus may be used in the treatment of cancers in which BIN1 can affect c-MYC, which is part of a biochemical cascade of events leading to tumor formation. The Ab3 antibodies may be useful for the same reason the Ab1 are useful. Other uses as research tools and as components for separation of Bin from other contaminants of living tissue, for example, are also contemplated for these antibodies.

V. Diagnostic Reagents and Methods

Advantageously, the present invention provides reagents and methods useful in detecting and diagnosing abnormal levels of Bau, and particularly deficiencies, mutant species, or excess production of either, in a patient. As defined herein, a deficiency of Bau is an inadequate amount of Bau to compensate for the levels of BIN1 and c-MYC in a patient. Conditions associated with deficiencies of Bau may include a variety of cancers, e.g., breast cancer, liver cancer and colon cancer, and hyperplastic disease states, e.g., benign prostate hyperplasia, involving MYC activation.

Thus, the proteins, protein fragments, antibodies, and polynucleotide sequences (including anti-sense polynucleotide sequences and oligonucleotide fragments), and Bau antisera and antibodies of this invention may be useful as diagnostic reagents. These reagents may optionally be labelled using diagnostic labels, such as radioactive labels, calorimetric enzyme label systems and the like conventionally used in diagnostic or therapeutic methods. Alternatively, the N- or C-terminus of Bau or a fragment thereof may be tagged with a viral epitope which can be recognized by a specific antisera. The reagents may be used to measure abnormal Bau levels in selected mammalian tissue in conventional diagnostic assays, e.g., Southern blotting, Northern and Western blotting, polymerase chain reaction (PCR), reverse transcriptase (RT) PCR, immunostaining, and the like. For example, in. biopsies of tumor tissue, loss of Bau expression in tumor tissue could be directly verified by RT-PCR or immunostaining. Alternatively, a Southern analysis, genomic PCR, or fluorescence in situ hybridization (FISH) may be performed to confirm Bau1 gene rearrangement.

In one example, as diagnostic agents the polynucleotide sequences may be employed to detect or quantitate normal Bau. The selection of the appropriate assay format and label system is within the skill of the art and may readily be chosen without requiring additional explanation by resort to the wealth of art in the diagnostic area.

Thus the present invention provides methods for the detection of disorders characterized by insufficient Bau levels. The methods involve contacting a selected mammalian tissue, e.g., a biopsy sample or other cells, with the selected reagent, protein, antisera antibody or DNA sequence, and measuring or detecting the amount of Bau present in the tissue in a selected assay format based on the binding or hybridization of the reagent to the tissue.

VI. Therapeutic Compositions and Methods

Compositions and methods useful for the treatment of conditions associated with inadequate Bau levels are provided. As stated above, included among such conditions are cancers involving MYC activation. Also provided are compositions and methods for inhibiting Bau activity in order to ameliorate a condition in which apoptosis is activated and BIN1 plays a role. Such conditions may include degenerative conditions, e.g., neurodegenerative diseases.

For example, where it is desirable to augment Bau activity in order to increase Bin1-mediated tumor suppressor activity or decrease the malignant activity of deregulated Myc, a therapeutic composition of the invention may be prepared which contains a Bau polypeptide, or a peptidomimetic drug derived from a Bau using the techniques described herein. Other Bau agonists, e.g., those identified using the methods described in Section VII below, are suitable components for a therapeutic composition which inhibits Bau activity. Such antagonists may be used in conjunction with Bau polypeptides or as alternatives thereto.

In other circumstances, such as degenerative diseases, it may be desirable to prepare therapeutic compositions which contain a Bau antagonist, such as a Bau antibody. One particularly desirable antibody would be directed against the Bin1-binding domain of Bau, located within aa 62 to 209 of SEQ ID NO:2. Other Bau antagonists, e.g., those identified using the methods described in Section VII below, may also be useful. Such antagonists may be used in conjunction with anti-Bau antibodies, or as alternatives thereto.

The therapeutic composition of the invention desirably contains 0.01 μg to 10 mg protein. These compositions may contain a pharmaceutically acceptable carrier. Suitable carriers are well known to those of skill in the art and include, for example, saline. Alternatively, such compositions may include conventional delivery systems into which protein of the invention is incorporated. Optionally, these compositions may contain other active ingredients, e.g., chemotherapeutics.

Still another method involves the use of the Bau polynucleotide sequences for gene therapy. In the method, the Bau sequences are introduced into a suitable vector for delivery to a cell containing a deficiency of Bau and/or BIN1 levels. By conventional genetic engineering techniques, the Bau gene sequence may be introduced to mutate the existing gene by recombination or to replace an inactive or missing gene.

Generally, a suitable polynucleotide-based treatment contains between $1 \times 10^{-3}$ pfu to $1 \times 10^{12}$ pfu per dose. However, the dose, timing and mode of administration of these compositions may be determined by one of skill in the art. Such factors as the age, condition, and the level of the Bau deficiency detected by the diagnostic methods described above, may be taken into account in determining the dose, timing and mode of administration of the therapeutic compositions of the invention. Generally, where treatment of an existing cancer or hyperplastic state is indicated, a therapeutic composition of the invention is preferably administered in a site-directed manner and is repeated as needed. Such therapy may be administered in conjunction with conventional therapies, including radiation and/or chemotherapeutic treatments.

VII. Drug Screening and Development

The proteins, antibodies and polynucleotide sequences of the present invention may also be used in the screening and development of chemical compounds or proteins which have utility as therapeutic drugs for the treatment of cancers characterized by Bau or BIN1, which regulate inappropriate MYC levels. As one example, a compound capable of binding to Bau and preventing its biological activity may be a useful drug component for the treatment or prevention of cancer. The methods described herein may also be applied to fragments of Bau. One particularly suitable fragment is the Bin1-binding domain (aa 62 to 209 of SEQ ID NO:2).

Suitable assay methods may be readily determined by one of skill in the art. Where desired, and depending on the assay selected, Bau may be immobilized directly or indirectly (e.g., via an anti-Bau antibody) on a suitable surface, e.g., in an ELISA format. Such immobilization surfaces are well known. For example, a wettable inert bead may be used. Alternatively, Bau may be used in screening assays which do not require immobilization, e.g., in the screening of combinatorial libraries.

Assays and techniques exist for the screening and development of drugs capable of binding to selected regions of Bau. These include the use of phage display system for expressing the Bau proteins, and using a culture of transfected *E. coli* or other microorganism to produce the proteins for binding studies of potential binding compounds. See, for example, the techniques described in G. Cesarini, *FEBS Letters*, 30(1):66–70 (July 1992); H. Gram et al., *J. Immunol. Meth.*, 161:169–176 (1993); C. Summer et al., *Proc. Natl. Acad. Sci., USA*, 89:3756–3760 (May 1992), incorporated by reference herein.

Other conventional drug screening techniques may be employed using the proteins, antibodies or polynucleotide sequences of this invention. As one example, a method for identifying compounds which specifically bind to a Bau protein can include simply the steps of contacting a selected Bau protein with a test compound to permit binding of the test compound to Bau; and determining the amount of test compound, if any, which is bound to the Bau protein. Such a method may involve the incubation of the test compound and the Bau protein immobilized on a solid support.

Typically, the surface containing the immobilized ligand is permitted to come into contact with a solution containing the Bau protein and binding is measured using an appropriate detection system. Suitable detection systems include the streptavidin horse radish peroxidase conjugate, direct conjugation by a tag, e.g., fluorescein. Other systems are well known to those of skill in the art. This invention is not limited by the detection system used.

Another method of identifying compounds which specifically bind to Bau can include the steps of contacting a Bau protein immobilized on a solid support with both a test compound and the protein sequence which is a receptor for Bau to permit binding of the receptor to the Bau protein; and determining the amount of the receptor which is bound to the Bau protein. The inhibition of binding of the normal protein by the test compound thereby indicates binding of the test compound to the Bau protein.

Thus, through use of such methods, the present invention is anticipated to provide compounds capable of interacting with Bau or portions thereof, and either enhancing or decreasing its biological activity, as desired. Such compounds are believed to be encompassed by this invention.

The assay methods described herein are also useful in screening for inhibition of the interaction between a Bau protein of the invention and BIN1 and/or another ligand(s). The solution containing the inhibitors may be obtained from any appropriate source, including, for example, extracts of supernatants from culture of bioorganisms, extracts from organisms collected from natural sources, chemical compounds, and mixtures thereof.

The following examples illustrate the isolation and use of the Bau nucleic acid sequences, polypeptides, and fragments of the invention. These examples are illustrative only and do not limit the scope of the invention.

EXAMPLE 1

Identification and Characterization of Bau

A yeast two hybrid screen was performed to identify U1-specific BINi-binding proteins.

The two hybrid system and methodology used for the screen was similar to that used to identify the MYC-interacting protein BIN1 [D. Sakamuro, et al, cited above]. A region of BIN1(aa 214–269 of SEQ ID NO:6) that included exon 9 (U1) and 10 sequences was used as the "bait" polypeptide. U1-binding clones were screened from a murine 10.5 d embryo cDNA library [Vojtek et al, Cell, 74: 205–214 (1993)] on the basis of their ability to confer HIS+ and LacZ+ phenotypes to the yeast assay strain L40, after transformation with "bait" and cDNA library plasmids. A mating strategy [Vojtek et al, Cell, 74:205–214 (1993)] was used to identify the U1-specific clones, using the control "baits" lamin, rhoB [Sakamuro et al, cited above], and a deletion mutant of the U1 region (containing only aa 214–229). cDNA library plasmids from U1-specific clones were shuttled into E. coli and subjected to DNA sequencing.

By this approach, two different sequences encoding U1-binding polypeptides were identified. One of the sequence classes encoded an N-terminal region of nucleophosmin, a growth-regulated protein which shuttles between the nucleolus and the nucleoplasm and is believed to play a role in the regulation of ribosome biosynthesis (Yung and Chou, Biochem. Biophys. Res. Comm., 217:313–325 (1995)]. Interestingly, oncogenic translocations of nucleophosmin occur in certain non-Hodgkin's lymphomas, and Myc is known to regulate ribosomal RNA synthesis.

The second sequence was unrelated to other sequences in the DNA database (data not shown). A ⁻1 kb near-full length cDNA was obtained from a murine embryonic phage library by standard hybridization methodology and its entire DNA sequence was determined (SEQ ID NO: 1). The DNA sequence of this clone, termed Bau (for Bin1-Associated U1-specific protein), encoded a 293 amino acid hydrophilic polypeptide of predicted molecular weight 34,137 Daltons (SEQ ID NO: 2). Structure prediction analysis of Bau using the COILS algorithm [A. Lupas, Meth Enz, 266: 513–525 (1996)] indicated that its N-terminal region (aa 1–160) is strongly predicted to form a coiled- coil domain (data not shown).

EXAMPLE 2

Bau Contains Motifs Found in Cysteine Protease Inhibitors and a Mitotic Checkpoint Regulator Comparison of Bau sequences to the DNA database revealed no significant relationship to known gene products. However, analysis of Bau sequence using the BLOCKS algorithm [Henikoff and Henikoff, Genomics. 19: 97–107 (1994)], which identifies signature motifs, turned up a region shared with type I cystatins, a class of cysteine protease inhibitors. (Signature motifs are sequence homology motifs that are found in all members of a polypeptide family with similar functional characteristics.) Type I cystatins are ⁻100 aa molecules that form non-disulfide linked dimers. The signature motif in Bau is located at aa 89–105 and was 65% (11/17) identical and 76% (13/17) similar to cystatin B [A. Machleidt et al., Biochem Biophys Res Commun, 131: 1187–1192 (1985)], a liver thiol protease inhibitor of the cystatin type I family most closely related to Bau.

The cystatin similarity suggests that Bau may be able to inhibit certain cysteine protease inhibitors. This is significant because (i.) a class of ubiquitous cysteine protease inhibitors termed caspases have a effector central role in activating apoptosis, and (ii.) Bin1 has been implicated in mediating apoptosis by Myc. Based on this relationship, Bau is hypothesized to function in a Bin1-Bau-caspase signaling pathway for apoptosis.

By visual inspection, an additional relationship was identified between the Bau-cystatin motif and the yeast checkpoint regulator Mad1p [Hardwick and Murray, J Cell Biol, 131: 709–720 (1995)]. Mad1p arrests mitosis in response to spindle assembly damage. Mad1p was one of a set of mitotic regulators that was examined for a suspected relationship to Bau, because of existing links between Bin1 and mitosis, namely, a localization of Bin1 at the microtubule organizing center (MTOC; spindle pole) during mitosis and an MTOC-like structure in cells destined to undergo apoptosis (G.P., unpublished observations). While it is not known yet if Bau has a mitotic role, or if Mad1p can inhibit cysteine protease activity, the Bau-cystatin motif identified in Mad1p is located at aa 83–103 and exhibits 57% (12/21) identity and 71% (15/21) similarity to the others. Bau and Mad1p also share similarity consisting of a polyasparagine region, at aa 165–169 and aa 330–372, respectively, downstream of the Bau-cystatin motif. Consistent with a functional link to apoptosis, spindle pole damage following loss of Mad1p results in an apoptosis-like death in yeast. Taken together, the structural relationship between Bau, type I cystatins, and Mad1p are consistent with a role for Bau in the regulation of Bin1-mediated apoptosis.

EXAMPLE 3

Bin1 Exons 9 (U1) and 10 are Necessary for Bau Interaction

The original two hybrid cDNAs encoded an open reading frame of at approximately 145 amino acids. This region, which constitutes a Bin1-binding domain (BBD) sufficient for Bin1 interaction, is located at aa 62–209 of Bau [SEQ ID NO:2].

To confirm the interaction between Bau and Bin1, and to define the exact regions of Bin1 required for interaction with Bau, the following in vitro biochemical analysis was performed. Various regions of Bin1, including U1, the adjacent NLS-like motif (exon 10 sequences), or U1-NLS, were expressed in E. coli by fusing them to glutathione-S-transferase (GST), using standard methodology. Unfused GST or GST fusions were purified by glutathione affinity purification, using standard methods, and employed for Bau binding experiments. Bau was engineered with a epitope tag and translation termination site at its 3' end; the Bau BBD was engineered for expression with a Kozak translation initiation site (the two hybrid cDNA subcloned included a termination site at its 3' end). For binding assays, equivalent amounts of GST proteins were mixed with $^{35}$S-methionine labeled Bau or BBD, expressed by in vitro translation in rabbit reticulocyte extracts.

Both Bau and the BBD were each observed to bind specifically to GST-U1-NLS but more poorly or not at all to GST-U1 or GST-NLS. The interaction of Bau was slightly weaker than BBD, which stable at near physiological salt concentrations (150 mM NaCl) and in 0.1% NP40 (a non-ionic detergent). In addition, under low salt conditions (50 mM NaCl), BBD could also bind weakly to GST-NLS, a region insufficient for Bau binding under any conditions. These data were confirmed for BBD in the two hybrid system.

The results indicated that Bau association depended upon both U1 and the NLS-like motif encoded by exon 10, which was spliced into Bin1 message following induction of either cell differentiation (in the absence of Myc) or apoptosis (in the presence of deregulated Myc). These findings supported the hypothesis that Bau may participate in mediating or regulating Bin1 function during such cell fate changes.

EXAMPLE 4

Bau is Encoded by a Single Copy, Evolutionarily Conserved Gene that is Widely Expressed To obtain evidence that Bau was a novel gene product, Southern and Northern analyses of genomic DNA and cytoplasmic RNA from murine and human cells were performed, using standard methods. Southern blots hybridized with the murine Bau cDNA revealed the presence of a single-copy bands in both murine and human DNA. The presence of evolutionarily conserved sequences strongly argued for gene identification. On Northern blots of RNA isolated from embryonic and adult murine tissues and from various human cell lines, a ubiquitously expressed RNA of approximately 1.4 kb was detected. In certain human tumor cells, such as HepG2 hepatocarcinoma cells, Bau message was not detected. Since normal murine liver expressed Bau, the lack of message in HepG2 cells suggested that Bau expression may be lost during the genesis of certain types of cancer such as hepatocarcinoma. Taken together, the data supported the assertion that Bau is encoded by a novel gene which has a tumor suppressor role like Bin1.

EXAMPLE 5

Bau Inhibits Malignant Cell Transformation

Bin1 can inhibit malignant cell transformation by Myc but also by the adenovirus E1A oncoprotein, through a Myc-independent mechanism [D. Sakamuro, et al., *Nature Genet*, 14: 69–77 (1996)]. Inhibition of Myc is partially dependent and E1A completely dependent upon the integrity of the U1 region in Bin1 [Elliott, Sakamuro et al., manuscript submitted]. Since Bau can interact with U1, we speculated that Bau might also inhibit cell transformation by Myc or E1A. To test this, Bau was assayed for the ability to suppress transformed focus formation in rat embryo fibroblasts (REFS) induced by these oncoproteins. Bau was subcloned into a mammalian expression vector so it could be tested in this assay. In addition, to assay any effect of the BBD, it was similarly subcloned for testing. As a negative control for any effects on transformation, we tested the effects of Bau or BBD on SV40 T antigen, which but is unaffected by Bin1 in this assay [D. Sakamuro, et al., cited above].

Bau and BBD was observed to inhibit the activity of E1A in this assay approximately 3-fold and 4-fold, respectively (see FIG. 1). While BBD suppressed the activity of Myc approximately 2-fold, Bau had a lesser effect that was not statistically significant (data not shown). This effect may reflect the lesser dependence of Myc for U1 in this assay. The inhibition of E1A was specific insofar as neither Bau nor BBD significantly affected transformation by T antigen. Consistent with a lack of inhibition in T antigen-transformed cells, exogenous message was detected in RNA isolated from pools of transformed colonies by Northern analysis. Taken together, the results supported the conclusion that Bau was a growth inhibitor that could interfere with certain types of malignant cell proliferation.

EXAMPLE 6

Isolation of Human Bau cDNA

Using the murine cDNA as a probe, the human Bau cDNA can be obtained from a human HeLa cell λZAPII cDNA library (Stratagene, La Jolla, Calif.) by standard methods [Sambrook et al, cited above], i.e., by hybridization with [$^{32}$P]-labeled Bau and washing under low stringency conditions (2XSSC 42° C.). The complete sequence of the human cDNA can be determined using the dideoxy method with Sequenase (US Biochemicals) and assembled and analyzed with MacVector software (IBI/Kodak).

EXAMPLE 7

Anti-Bau Antibodies

For use in generating antibodies, the Bau sequences encoding the Bin1-binding domain (BBD, aa 62 to 209 of SEQ ID NO:2) was expressed as a glutathione-S-transferase (GST) fusion protein.

To construct the GST fusion protein, the partial Bau CDNA initially isolated in the two hybrid screen was used (this cDNA encoded only the BBD as defined above). A Bam HI-Eco RI fragment including the partial cDNA was isolated from the two hybrid vector and shuttled into the baculovirus recombination vector pAcGHLT-C (Invitrogen, Inc., San Diego, Calif.). The recombinant plasmid was introduced into Sf9 insect cells. The GST-Bau$_{62-209}$ polypeptide whose synthesis was directed by the recombinant plasmid was purified from Sf9 cell extracts on glutathione-Sepharose (Pharmacia), using protocols supplied by the vendor.

To generate BBD-specific antibodies, GST-Bau$_{62-209}$ was used to immunize mice. Cells prepared from the spleens of immunized mice were processed for hybridoma production and monoclonal antibody purification, using standard protocols.

All documents cited above are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

What is claimed is:

1. An isolated mammalian BIN1-Associated U1-specific (Bau) polypeptide, said polypeptide selected from the group consisting of:
   (a) murine Bau, SEQ ID NO:2;
   (b) a mammalian sequence at least 90% identical with the full-length sequence of SEQ ID NO:2 as determined by the WU-BLAST 2 algorithm and wherein said mammalian sequence has Bau biological activity; and
   (c) a fragment of (a) or (b) having Bau biological activity.

2. An isolated mammalian BIN1-Associated U1-specific (Bau) polypeptide, wherein said polypeptide is selected from the group consisting of:
   (a) aa 62 to 209 of SEQ ID NO:2; and
   (b) aa 1 to 60 of SEQ ID NO:2.

* * * * *

UNITED STATES PATENT AND TRADEMARK OFFICE
CERTIFICATE OF CORRECTION

PATENT NO. : 6,140,465
DATED : December 14, 2000
INVENTOR(S) : George C. Prendergast It is certified that error appears in the above-indentified patent and that said Letters Patent is hereby corrected as shown below:

Column 1, line 5, replace "Aug. 29, 1997" with -- Aug. 29, 1996 --.

Column 5, line 13, replace "c-mYc." with -- c-Myc. --.

Column 7, line 29, replace "(CDRS)" with -- (CDRs) --.

Column 8, line 37, delete the period "(.)" after the "in" --.

Column 10, line 12, replace "30" with -- 307 --.

Column 12, line 3, replace "Madip" with -- Mad1p --.

Column 13, line 32, replace "(REFS)" with -- (REFs) --.

Column 14, line 30, replace "CDNA" with -- cDNA --.

Col. 28, line 65, replace "60" with -- 160 --.

Signed and Sealed this

Fifteenth Day of May, 2001

*Attest:*

NICHOLAS P. GODICI

*Attesting Officer*  *Acting Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 926 base pairs
      (B) TYPE: nucleic acid (C) STRANDEDNESS: double
            (D) TOPOLOGY: unknown (ii) MOLECULE TYPE: cDNA (ix) FEATURE:
            (A) NAME/KEY: CDS
            (B) LOCATION: 48..926

(xi) SEQUENCE DESCRIPTION: SEQ ID NO:1:

```
GGGGTGACGT GGCCATTGAG GTCTTTGAGC TGCCTGAGAA CGAGGAC ATG TTT TCC          56
                                                  Met Phe Ser
                                                   1

CCA TCT GAC CTG GAC ACA AGC AAG CTC AGC CAC AAG TTC AAA GAG TTG         104
Pro Ser Asp Leu Asp Thr Ser Lys Leu Ser His Lys Phe Lys Glu Leu
    5                  10                  15

CAA ATC AAA CAT GCA GTT ACA GAA GCA GAG ATT CAA AAA TTG AAG ACC         152
Gln Ile Lys His Ala Val Thr Glu Ala Glu Ile Gln Lys Leu Lys Thr
 20                  25                  30                  35

AAG CTT CAA GCA TCC GAA AAT GAG AAA GTA AGG TGG GAA CTA GAA AAG         200
Lys Leu Gln Ala Ser Glu Asn Glu Lys Val Arg Trp Glu Leu Glu Lys
                 40                  45                  50

AAC CAA CTG CAA CAG AAT ATA GAA GAG AAT AAA GAA CGG ATG CTG AAG         248
Asn Gln Leu Gln Gln Asn Ile Glu Glu Asn Lys Glu Arg Met Leu Lys
             55                  60                  65

TTG GAG AGC TAC TGG ATC GAG GCT CAG ACA TTA TGT CAT ACG GTG AAT         296
Leu Glu Ser Tyr Trp Ile Glu Ala Gln Thr Leu Cys His Thr Val Asn
         70                  75                  80

GAG CAT CTC AAA GAG ACT CAG AGC CAG TAC CAA GCC CTG GAA AAG AAA         344
Glu His Leu Lys Glu Thr Gln Ser Gln Tyr Gln Ala Leu Glu Lys Lys
     85                  90                  95

TAC AAC AAA GCA AAG AAG CTG ATC AAA GAC TTC CAG CAA AAA GAG CTC         392
Tyr Asn Lys Ala Lys Lys Leu Ile Lys Asp Phe Gln Gln Lys Glu Leu
100                 105                 110                 115

GAT TTC ATC AAG AGA CAG GAA GTA GAA AGA AAG AAG CGG GAG GAG GTG         440
Asp Phe Ile Lys Arg Gln Glu Val Glu Arg Lys Lys Arg Glu Glu Val
                120                 125                 130

GAA AAG GCT CAC CTG CTT GAA GTC CAA GGC CTG CAA GTT CGG ATT AGA         488
Glu Lys Ala His Leu Leu Glu Val Gln Gly Leu Gln Val Arg Ile Arg
            135                 140                 145

GAT TTG GAG GCT GAG GTG TTC AGA CTA CTA AAG CAA AAT GGG ACC CAG         536
Asp Leu Glu Ala Glu Val Phe Arg Leu Leu Lys Gln Asn Gly Thr Gln
        150                 155                 160

GTT AAC AAC AAC AAC AAC ATC TTT GAG AGA AGA CCA TCT CCC GGG GAA         584
Val Asn Asn Asn Asn Asn Ile Phe Glu Arg Arg Pro Ser Pro Gly Glu
    165                 170                 175

GTC TCG AAA GGA GAC ACT ATG GAG AAT GTG GAA GTC AAG CAA ACA TCC         632
Val Ser Lys Gly Asp Thr Met Glu Asn Val Glu Val Lys Gln Thr Ser
180                 185                 190                 195

TGT CAG GAC GGC TTG AGC CAA GAC CTG AAT GAA GCA GTC CCA GAG ACA         680
Cys Gln Asp Gly Leu Ser Gln Asp Leu Asn Glu Ala Val Pro Glu Thr
                200                 205                 210

GAG CGC CTG GAT TCG AAA GCA TTG AAA ACC CGG GCC CAG CTC TCT GTG         728
Glu Arg Leu Asp Ser Lys Ala Leu Lys Thr Arg Ala Gln Leu Ser Val
            215                 220                 225

AAG AAC AGG CGC CAG AGG CCC ACA AGG ACA CGG CTC TAT GAC AGC GTC         776
Lys Asn Arg Arg Gln Arg Pro Thr Arg Thr Arg Leu Tyr Asp Ser Val
        230                 235                 240

AGC TCA ACT GAT GGG GAG GAC AGC CTG GAG AGG AAG GTG AGC ACT CTC         824
Ser Ser Thr Asp Gly Glu Asp Ser Leu Glu Arg Lys Val Ser Thr Leu
    245                 250                 255
```

```
AAT GGC TGG CAG ACT CTT GCA GAG TGT CGT TGT CCA CCA GTG TAT TTA        872
Asn Gly Trp Gln Thr Leu Ala Glu Cys Arg Cys Pro Pro Val Tyr Leu
260                 265                 270                 275

TTG AAC GTG ATA GCG GTT TTA CTG ATC TGT GCC TTA CTT GGA AGA AAG        920
Leu Asn Val Ile Ala Val Leu Leu Ile Cys Ala Leu Leu Gly Arg Lys
                280                 285                 290

TCT CCC                                                                926
Ser Pro
```

(2) INFORMATION FOR SEQ ID NO:2:

(i) SEQUENCE CHARACTERISTICS:
        (A) LENGTH: 293 amino acids
        (B) TYPE: amino acid
        (D) TOPOLOGY: linear (ii) MOLECULE TYPE: protein (xi) SEQUENCE DESCRIPTION: SEQ ID NO:2:

```
Met Phe Ser Pro Ser Asp Leu Asp Thr Ser Lys Leu Ser His Lys Phe
1               5                   10                  15

Lys Glu Leu Gln Ile Lys His Ala Val Thr Glu Ala Glu Ile Gln Lys
                20                  25                  30

Leu Lys Thr Lys Leu Gln Ala Ser Glu Asn Glu Lys Val Arg Trp Glu
            35                  40                  45

Leu Glu Lys Asn Gln Leu Gln Gln Asn Ile Glu Glu Asn Lys Glu Arg
        50                  55                  60

Met Leu Lys Leu Glu Ser Tyr Trp Ile Glu Ala Gln Thr Leu Cys His
65                  70                  75                  80

Thr Val Asn Glu His Leu Lys Glu Thr Gln Ser Gln Tyr Gln Ala Leu
                85                  90                  95

Glu Lys Lys Tyr Asn Lys Ala Lys Lys Leu Ile Lys Asp Phe Gln Gln
                100                 105                 110

Lys Glu Leu Asp Phe Ile Lys Arg Gln Glu Val Glu Arg Lys Lys Arg
            115                 120                 125

Glu Glu Val Glu Lys Ala His Leu Leu Glu Val Gln Gly Leu Gln Val
130                 135                 140

Arg Ile Arg Asp Leu Glu Ala Glu Val Phe Arg Leu Leu Lys Gln Asn
145                 150                 155                 160

Gly Thr Gln Val Asn Asn Asn Asn Ile Phe Glu Arg Arg Pro Ser
                165                 170                 175

Pro Gly Glu Val Ser Lys Gly Asp Thr Met Glu Asn Val Glu Val Lys
                180                 185                 190

Gln Thr Ser Cys Gln Asp Gly Leu Ser Gln Asp Leu Asn Glu Ala Val
            195                 200                 205

Pro Glu Thr Glu Arg Leu Asp Ser Lys Ala Leu Lys Thr Arg Ala Gln
210                 215                 220

Leu Ser Val Lys Asn Arg Arg Gln Arg Pro Thr Arg Thr Arg Leu Tyr
225                 230                 235                 240

Asp Ser Val Ser Ser Thr Asp Gly Glu Asp Ser Leu Glu Arg Lys Val
                245                 250                 255

Ser Thr Leu Asn Gly Trp Gln Thr Leu Ala Glu Cys Arg Cys Pro Pro
                260                 265                 270

Val Tyr Leu Leu Asn Val Ile Ala Val Leu Leu Ile Cys Ala Leu Leu
            275                 280                 285

Gly Arg Lys Ser Pro
            290
```

(2) INFORMATION FOR SEQ ID NO:3:

(i) SEQUENCE CHARACTERISTICS:
        (A) LENGTH: 402 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..399

(ix) FEATURE:
        (A) NAME/KEY: mat_peptide
        (B) LOCATION: 1

(xi) SEQUENCE DESCRIPTION: SEQ ID NO:3:

```
GAG ATC AGA GTG AAC CAT GAG CCA GAG CCG GCC AGT GGG GCC TCA CCC      48
Glu Ile Arg Val Asn His Glu Pro Glu Pro Ala Ser Gly Ala Ser Pro
  1               5                  10                  15

GGG GCT GCC ATC CCC AAG TCC CCA TCT CAG CCA GCA GAG GCC TCC GAG      96
Gly Ala Ala Ile Pro Lys Ser Pro Ser Gln Pro Ala Glu Ala Ser Glu
             20                  25                  30

GTG GTG GGT GGA GCC CAG GAG CCA GGG GAG ACA GCA GCC AGT GAA GCA     144
Val Val Gly Gly Ala Gln Glu Pro Gly Glu Thr Ala Ala Ser Glu Ala
         35                  40                  45

ACC TCC AGC TCT CTT CCG GCT GTG GTG GTG GAG ACC TTC TCC GCA ACT     192
Thr Ser Ser Ser Leu Pro Ala Val Val Val Glu Thr Phe Ser Ala Thr
     50                  55                  60

GTG AAT GGG GCG GTG GAG GGC AGC GCT GGG ACT GGA CGC TTG GAC CTG     240
Val Asn Gly Ala Val Glu Gly Ser Ala Gly Thr Gly Arg Leu Asp Leu
 65                  70                  75                  80

CCC CCG GGA TTC ATG TTC AAG GTT CAA GCC CAG CAT GAT TAC ACG GCC     288
Pro Pro Gly Phe Met Phe Lys Val Gln Ala Gln His Asp Tyr Thr Ala
                 85                  90                  95

ACT GAC ACT GAT GAG CTG CAA CTC AAA GCT GGC GAT GTG GTG TTG GTG     336
Thr Asp Thr Asp Glu Leu Gln Leu Lys Ala Gly Asp Val Val Leu Val
            100                 105                 110

ATT CCT TTC CAG AAC CCA GAG GAG CAG GAT GAA GGC TGG CTC ATG GGT     384
Ile Pro Phe Gln Asn Pro Glu Glu Gln Asp Glu Gly Trp Leu Met Gly
        115                 120                 125

GTG AAG GAG AGC GAC TGA                                             402
Val Lys Glu Ser Asp
    130
```

(2) INFORMATION FOR SEQ ID NO:4:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:4:

```
Glu Ile Arg Val Asn His Glu Pro Glu Pro Ala Ser Gly Ala Ser Pro
  1               5                  10                  15

Gly Ala Ala Ile Pro Lys Ser Pro Ser Gln Pro Ala Glu Ala Ser Glu
             20                  25                  30

Val Val Gly Gly Ala Gln Glu Pro Gly Glu Thr Ala Ala Ser Glu Ala
         35                  40                  45
```

```
Thr Ser Ser Ser Leu Pro Ala Val Val Glu Thr Phe Ser Ala Thr
         50                  55                  60

Val Asn Gly Ala Val Glu Gly Ser Ala Gly Thr Gly Arg Leu Asp Leu
 65                  70                  75                  80

Pro Pro Gly Phe Met Phe Lys Val Gln Ala Gln His Asp Tyr Thr Ala
                 85                  90                  95

Thr Asp Thr Asp Glu Leu Gln Leu Lys Ala Gly Asp Val Leu Val
            100                 105                 110

Ile Pro Phe Gln Asn Pro Glu Glu Gln Asp Gly Gly Trp Leu Met Gly
            115                 120                 125

Val Lys Glu Ser Asp
    130
```

(2) INFORMATION FOR SEQ ID NO:5:

(i) SEQUENCE CHARACTERISTICS:
        (A) LENGTH: 1925 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 60..1412

(ix) FEATURE:
        (A) NAME/KEY: mat_peptide
        (B) LOCATION: 60

(xi) SEQUENCE DESCRIPTION: SEQ ID NO:5:

```
GAATTCCGTG CTGGTTGAGC TTGCTCATCT CCTTGTGGAA GTTTTCCTCC AGGCCCGCG        59

ATG CTC TGG AAC GTG GTG ACG GCG GGA AAG ATC GCC AGC AAC GTG CAG        107
Met Leu Trp Asn Val Val Thr Ala Gly Lys Ile Ala Ser Asn Val Gln
  1               5                  10                  15

AAG AAG CTC ACC CGC GCG CAG GAG AAG GTT CTC CAG AAG CTG GGG AAG        155
Lys Lys Leu Thr Arg Ala Gln Glu Lys Val Leu Gln Lys Leu Gly Lys
             20                  25                  30

GCA GAT GAG ACC AAG GAT GAG CAG TTT GAG CAG TGC GTC CAG AAT TTC        203
Ala Asp Glu Thr Lys Asp Glu Gln Phe Glu Gln Cys Val Gln Asn Phe
         35                  40                  45

AAC AAG CAG CTG ACG GAG GGC ACC CGG CTG CAG AAG GAT CTC CGG ACC        251
Asn Lys Gln Leu Thr Glu Gly Thr Arg Leu Gln Lys Asp Leu Arg Thr
     50                  55                  60

TAC CTG GCC TCC GTC AAA GCC ATG CAC GAG GCT TCC AAG AAG CTG AAT        299
Tyr Leu Ala Ser Val Lys Ala Met His Glu Ala Ser Lys Lys Leu Asn
 65                  70                  75                  80

GAG TGT CTG CAG GAG GTG TAT GAG CCC GAT TGG CCC GGC AGG GAT GAG        347
Glu Cys Leu Gln Glu Val Tyr Glu Pro Asp Trp Pro Gly Arg Asp Glu
                 85                  90                  95

GCA AAC AAG ATC GCA GAG AAC AAC GAC CTG CTG TGG ATG GAT TAC CAC        395
Ala Asn Lys Ile Ala Glu Asn Asn Asp Leu Leu Trp Met Asp Tyr His
            100                 105                 110

CAG AAG CTG GTG GAC CAG GCG CTG CTG ACC ATG GAC ACG TAC CTG GGC        443
Gln Lys Leu Val Asp Gln Ala Leu Leu Thr Met Asp Thr Tyr Leu Gly
        115                 120                 125

CAG TTC CCC GAC ATC AAG TCA CGC ATT GCC AAG CGG GGG CGC AAG CTG        491
Gln Phe Pro Asp Ile Lys Ser Arg Ile Ala Lys Arg Gly Arg Lys Leu
    130                 135                 140

GTG GAC TAC GAC AGT GCC CGG CAC CAC TAC GAG TCC CTT CAA ACT GCC        539
Val Asp Tyr Asp Ser Ala Arg His His Tyr Glu Ser Leu Gln Thr Ala
```

```
                     145                 150                 155                 160
AAA AAG AAG GAT GAA GCC AAA ATT GCC AAG GCC GAG GAG GAG CTC ATC                 587
Lys Lys Lys Asp Glu Ala Lys Ile Ala Lys Ala Glu Glu Glu Leu Ile
                165                 170                 175

AAA GCC CAG AAG GTG TTT GAG GAG ATG AAT GTG GAT CTG CAG GAG GAG                 635
Lys Ala Gln Lys Val Phe Glu Glu Met Asn Val Asp Leu Gln Glu Glu
            180                 185                 190

CTG CCG TCC CTG TGG AAC AGC CGC GTA GGT TTC TAC GTC AAC ACG TTC                 683
Leu Pro Ser Leu Trp Asn Ser Arg Val Gly Phe Tyr Val Asn Thr Phe
        195                 200                 205

CAG AGC ATC GCG GGC CTG GAG GAA AAC TTC CAC AAG GAG ATG AGC AAG                 731
Gln Ser Ile Ala Gly Leu Glu Glu Asn Phe His Lys Glu Met Ser Lys
    210                 215                 220

CTC AAC CAG AAC CTC AAT GAT GTG CTG GTC GGC CTG GAG AAG CAA CAC                 779
Leu Asn Gln Asn Leu Asn Asp Val Leu Val Gly Leu Glu Lys Gln His
225                 230                 235                 240

GGG AGC AAC ACC TTC ACG GTC AAG GCC CAG CCC AGA AAG AAA AGT AAA                 827
Gly Ser Asn Thr Phe Thr Val Lys Ala Gln Pro Arg Lys Lys Ser Lys
                245                 250                 255

CTG TTT TCG CGG CTG CGC AGA AAG AAG AAC AGT GAC AAC GCG CCT GCA                 875
Leu Phe Ser Arg Leu Arg Arg Lys Lys Asn Ser Asp Asn Ala Pro Ala
            260                 265                 270

AAA GGG AAC AAG AGC CCT TCG CCT CCA GAT GGC TCC CCT GCC GCC ACC                 923
Lys Gly Asn Lys Ser Pro Ser Pro Pro Asp Gly Ser Pro Ala Ala Thr
        275                 280                 285

CCC GAG ATC AGA GTC AAC CAC GAG CCA GAG CCG GCC GGC GGG GCC ACG                 971
Pro Glu Ile Arg Val Asn His Glu Pro Glu Pro Ala Gly Gly Ala Thr
    290                 295                 300

CCC GGG GCC ACC CTC CCC AAG TCC CCA TCT CAG CCA GCA GAG GCC TCG                1019
Pro Gly Ala Thr Leu Pro Lys Ser Pro Ser Gln Pro Ala Glu Ala Ser
305                 310                 315                 320

GAG GTG GCG GGT GGG ACC CAA CCT GCG GCT GGA GCC CAG GAG CCA GGG                1067
Glu Val Ala Gly Gly Thr Gln Pro Ala Ala Gly Ala Gln Glu Pro Gly
                325                 330                 335

GAG ACT TCT GCA AGT GAA GCA GCC TCC AGC TCT CTT CCT GCT GTC GTG                1115
Glu Thr Ser Ala Ser Glu Ala Ala Ser Ser Ser Leu Pro Ala Val Val
            340                 345                 350

GTG GAG ACC TTC CCA GCA ACT GTG AAT GGC ACC GTG GAG GGC GGC AGT                1163
Val Glu Thr Phe Pro Ala Thr Val Asn Gly Thr Val Glu Gly Gly Ser
        355                 360                 365

GGG GCC GGG CGC TTG GAC CTG CCC CCA GGT TTC ATG TTC AAG GTA CAG                1211
Gly Ala Gly Arg Leu Asp Leu Pro Pro Gly Phe Met Phe Lys Val Gln
    370                 375                 380

GCC CAG CAC GAC TAC ACG GCC ACT GAC ACA GAC GAG CTG CAG CTC AAG                1259
Ala Gln His Asp Tyr Thr Ala Thr Asp Thr Asp Glu Leu Gln Leu Lys
385                 390                 395                 400

GCT GGT GAT GTG GTG CTG GTG ATC CCC TTC CAG AAC CCT GAA GAG CAG                1307
Ala Gly Asp Val Val Leu Val Ile Pro Phe Gln Asn Pro Glu Glu Gln
                405                 410                 415

GAT GAA GGC TGG CTC ATG GGC GTG AAG GAG AGC GAC TGG AAC CAG CAC                1355
Asp Glu Gly Trp Leu Met Gly Val Lys Glu Ser Asp Trp Asn Gln His
            420                 425                 430

AAG AAG CTG GAG AAG TGC CGT GGC GTC TTC CCC GAG AAC TTC ACT GAG                1403
Lys Lys Leu Glu Lys Cys Arg Gly Val Phe Pro Glu Asn Phe Thr Glu
        435                 440                 445

AGG GTC CCA TGACGGCGGG GCCCAGGCAG CCTCCGGGCG TGTGAAGAAC                        1452
Arg Val Pro
    450

ACCTCCTCCC GAAAAATGTG TGGTTCTTTT TTTTGTTTTG TTTTCGTTTT TCATCTTTTG              1512
```

```
AAGAGCAAAG GGAAATCAAG AGGAGACCCC CAGGCAGAGG GGCGTTCTCC CAAAGTTTAG    1572

GTCGTTTTCC AAAGAGCCGC GTCCCGGCAA GTCCGGCGGA ATTCACCAGT GTTCCTGAAG    1632

CTGCTGTGTC CTCTAGTTGA GTTTCTGGCG CCCCTGCCTG TGCCCGCATG TGTGCCTGGC    1692

CGCAGGGCGG GGCTGGGGGC TGCCGAGCCA CCATACTTAA CTGAAGCTTC GGCCGCACCA    1752

CCCGGGGAAG GGTCCTCTTT TCCTGGCAGC TGCTGTGGGT GGGGCCCAGA CACCAGCCTA    1812

GCCTGCTCTG CCCCGCAGAC GGTCTGTGTG CTGTTTGAAA ATAAATCTTA GTGTTCAAAA    1872

CAAAATGAAA CAAAAAAAAA AATGATAAAA ACTCTCAAAA AACAAGGAA TTC            1925
```

(2) INFORMATION FOR SEQ ID NO:6:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Trp Asn Val Val Thr Ala Gly Lys Ile Ala Ser Asn Val Gln
 1               5                  10                  15

Lys Lys Leu Thr Arg Ala Gln Glu Lys Val Leu Gln Lys Leu Gly Lys
            20                  25                  30

Ala Asp Glu Thr Lys Asp Glu Gln Phe Glu Gln Cys Val Gln Asn Phe
        35                  40                  45

Asn Lys Gln Leu Thr Glu Gly Thr Arg Leu Gln Lys Asp Leu Arg Thr
    50                  55                  60

Tyr Leu Ala Ser Val Lys Ala Met His Glu Ala Ser Lys Lys Leu Asn
65                  70                  75                  80

Glu Cys Leu Gln Glu Val Tyr Glu Pro Asp Trp Pro Gly Arg Asp Glu
                85                  90                  95

Ala Asn Lys Ile Ala Glu Asn Asn Asp Leu Leu Trp Met Asp Tyr His
            100                 105                 110

Gln Lys Leu Val Asp Gln Ala Leu Leu Thr Met Asp Thr Tyr Leu Gly
        115                 120                 125

Gln Phe Pro Asp Ile Lys Ser Arg Ile Ala Lys Arg Gly Arg Lys Leu
    130                 135                 140

Val Asp Tyr Asp Ser Ala Arg His His Tyr Glu Ser Leu Gln Thr Ala
145                 150                 155                 160

Lys Lys Lys Asp Glu Ala Lys Ile Ala Lys Ala Glu Glu Glu Leu Ile
                165                 170                 175

Lys Ala Gln Lys Val Phe Glu Glu Met Asn Val Asp Leu Gln Glu Glu
            180                 185                 190

Leu Pro Ser Leu Trp Asn Ser Arg Val Gly Phe Tyr Val Asn Thr Phe
        195                 200                 205

Gln Ser Ile Ala Gly Leu Glu Glu Asn Phe His Lys Glu Met Ser Lys
    210                 215                 220

Leu Asn Gln Asn Leu Asn Asp Val Leu Val Gly Leu Glu Lys Gln His
225                 230                 235                 240

Gly Ser Asn Thr Phe Thr Val Lys Ala Gln Pro Arg Lys Lys Ser Lys
                245                 250                 255

Leu Phe Ser Arg Leu Arg Arg Lys Lys Asn Ser Asp Asn Ala Pro Ala
            260                 265                 270

Lys Gly Asn Lys Ser Pro Ser Pro Pro Asp Gly Ser Pro Ala Ala Thr
```

-continued

```
                   275                 280                 285
    Pro Glu Ile Arg Val Asn His Glu Pro Glu Pro Ala Gly Gly Ala Thr
                    290             295             300
    Pro Gly Ala Thr Leu Pro Lys Ser Pro Ser Gln Pro Ala Glu Ala Ser
    305                 310             315                 320
    Glu Val Ala Gly Gly Thr Gln Pro Ala Ala Gly Ala Gln Glu Pro Gly
                    325                 330             335
    Glu Thr Ser Ala Ser Glu Ala Ala Ser Ser Leu Pro Ala Val Val
                    340             345             350
    Val Glu Thr Phe Pro Ala Thr Val Asn Gly Thr Val Glu Gly Gly Ser
                355             360             365
    Gly Ala Gly Arg Leu Asp Leu Pro Pro Gly Phe Met Phe Lys Val Gln
        370             375             380
    Ala Gln His Asp Tyr Thr Ala Thr Asp Thr Asp Glu Leu Gln Leu Lys
    385             390             395             400
    Ala Gly Asp Val Val Leu Val Ile Pro Phe Gln Asn Pro Glu Glu Gln
                    405             410             415
    Asp Glu Gly Trp Leu Met Gly Val Lys Glu Ser Asp Trp Asn Gln His
                420             425             430
    Lys Lys Leu Glu Lys Cys Arg Gly Val Phe Pro Glu Asn Phe Thr Glu
                435             440             445
    Arg Val Pro
    450
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:7:

```
Leu Xaa Gly Xaa Glu
1               5
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:8:

```
Leu Xaa Cys Xaa Glu
1               5
```